United States Patent [19]
Cary, III

[11] Patent Number: 5,891,139
[45] Date of Patent: Apr. 6, 1999

[54] SAFE USE FULLY DISPOSABLE ELECTROLYSIS NEEDLE ASSEMBLY

[76] Inventor: Harry W. Cary, III, 49 Arnold St., Riverside, R.I. 02915

[21] Appl. No.: 931,663

[22] Filed: Sep. 16, 1997

[51] Int. Cl.⁶ .................................................. A61B 17/41
[52] U.S. Cl. ............................................. 606/44; 606/36
[58] Field of Search ........................... 606/36, 44, 32, 606/131, 133

[56] References Cited

U.S. PATENT DOCUMENTS

| | | | |
|---|---|---|---|
| 1,781,362 | 11/1930 | Brigida | 606/44 |
| 2,994,324 | 8/1961 | Lemos | 606/44 |
| 4,785,808 | 11/1988 | Cary | 606/44 |

*Primary Examiner*—Glenn K. Dawson
*Attorney, Agent, or Firm*—Robert J. Doherty

[57] ABSTRACT

An electrolysis needle assembly having a shank for attachment to an electrolysis handle which includes an air flow source and a forward portion from which the needle extends. Each is provided with an air flow slot so as to enable air to be directed from the handle along the needle assembly to the skin of the patient and in which a needle protective cap is provided for such forward end. The cap is used to manipulate the assembly as in attaching and removing the needle from the electrolysis handle.

6 Claims, 4 Drawing Sheets

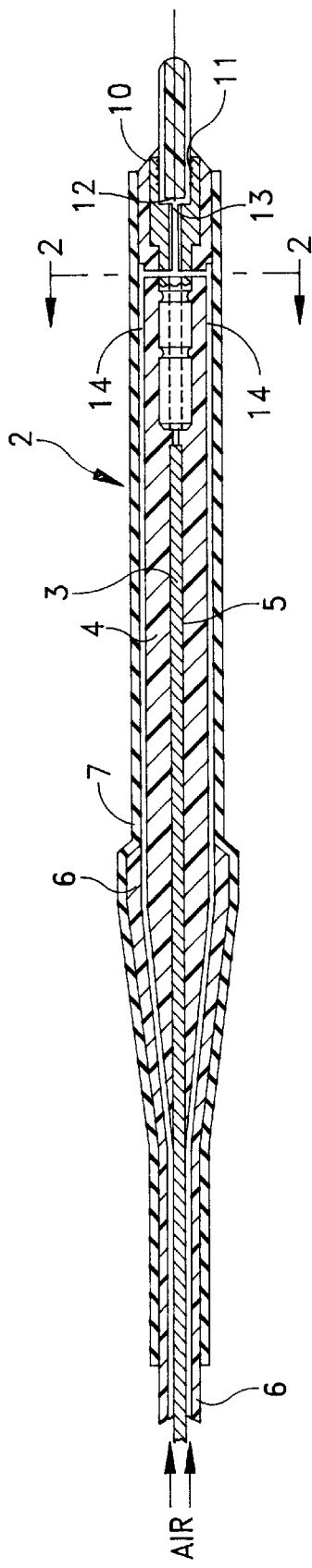
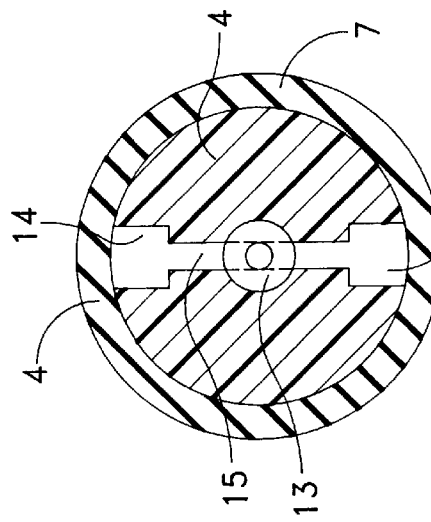

SAFE USE FULLY DISPOSABLE ELECTROLYSIS NEEDLE ASSEMBLY

FIELD OF THE INVENTION

The present invention relates to improvements in the construction of fully disposable electrolysis needle assemblies utilized in removing unwanted hair.

BACKGROUND AND OBJECTS OF THE INVENTION

The majority of presently utilized electrolysis needles are of the re-sterilizable type and include an extremely fine tip or blade constructed of surgical steel wire which is adapted to be inserted into a hair follicle of a patient along side a hair shaft in the dermis. This fine tipped portion is mechanically clenched or otherwise attached to a larger shank portion and in turn is adapted to be received into an electrical connection socket in the hand held instrument portion of an overall electrolysis device. A description of such prior art needles and electrolysis machines is set forth in U.S. Pat. No. 4,785,808 issued Nov. 22, 1988 to the present inventor. The specification of U.S. Pat. No. 4,785,808 is hereby incorporated into the present application by specific reference thereto.

Electrolysis machines also in some cases incorporate a source of pressurized air generated in the machine itself or elsewhere and direct a flow of such air through the instrument body and thence along or close to the needle so as to contact the area of the patient's skin adjacent the point of penetration to cool the skin or otherwise distract the patient from the slight discomfort produced by such process. In such air flow procedures, it is a simple matter to regulate the flow of such by modifying the hole size in the end of the protective cap through which the fine needle projects, that is, the opening between the cap and needle is adjusted larger or smaller dependent upon the amount of air flow desired.

Such re-sterilizable needles include a number of disadvantages as set forth in the above referred to patent and, accordingly, fully disposable needle assemblies in which the needle is embedded within a plastic body so as to form, in effect, a one-piece construction which after use is discarded have become increasingly desirable. Such one-piece needle assemblies are as explained in the aforementioned patent provided with a rearwardly extending shank portion which extends into a forwardly disposed receiving socket at the forward end of the hand held portion of the electrolysis instrument. With such constructions, however, there are no means to provide the aforementioned cooling and/or distracting air flow adjacent the patient's skin and, accordingly, such effect would be desirable as an object of the present invention.

A further object of the present invention is the provision of a system and apparatus by which completely disposable needle assemblies such as described in the aforementioned patent may be more easily removed from the hand held electrolysis unit such that the operator has less likelihood of coming in contact with the needle portion of the needle assembly which after use must be considered contaminated under today's procedures.

These and other objects of the present invention are accomplished by the provision of a disposable, single use, throw away electrolysis needle assembly having a forward portion from which a needle forwardly projects, a shank portion disposed rearwardly thereof and adapted to contact the face of the electrolysis instrument handle surrounding the needle assembly receiving socket thereof and a rearwardly extending shank portion adapted to extend into and be connected with the socket and wherein at least the shank portion and flange are provided with at least one radially inwardly extending channel such that air from a pressurized air source existing in the socket may pass through said needle assembly so as to contact the skin of the human patient adjacent the contact point of the needle therewith and further in which a hollow tubular safety cap is provided for fitment over the forward end of the needle assembly and by which the needle assembly may be inserted and withdrawn by the hand held portion of the electrolysis body itself and which is subsequently disposed along with the needle assembly while such protective cap is positioned on the forward end of the needle body and thus covers the forwardly extending needle portion thereof.

Other objects, features and advantages of the invention shall become apparent as the description thereof proceeds when considered in connection with the accompanying illustrative drawings.

DESCRIPTION OF THE DRAWINGS

In the drawings which illustrate the best mode presently contemplated for carrying out the present invention:

FIG. 1 is an overall elevational view with parts broken away for purposes of clarity showing the front end portion, that is, the hand held portion, of an electrolysis machine which is modified to incorporate the safety system and one piece disposable needle assembly of the present invention;

FIG. 2 is a sectional view along the line 2—2 of FIG. 1;

DETAILED DESCRIPTION OF THE INVENTION

Figure 3:
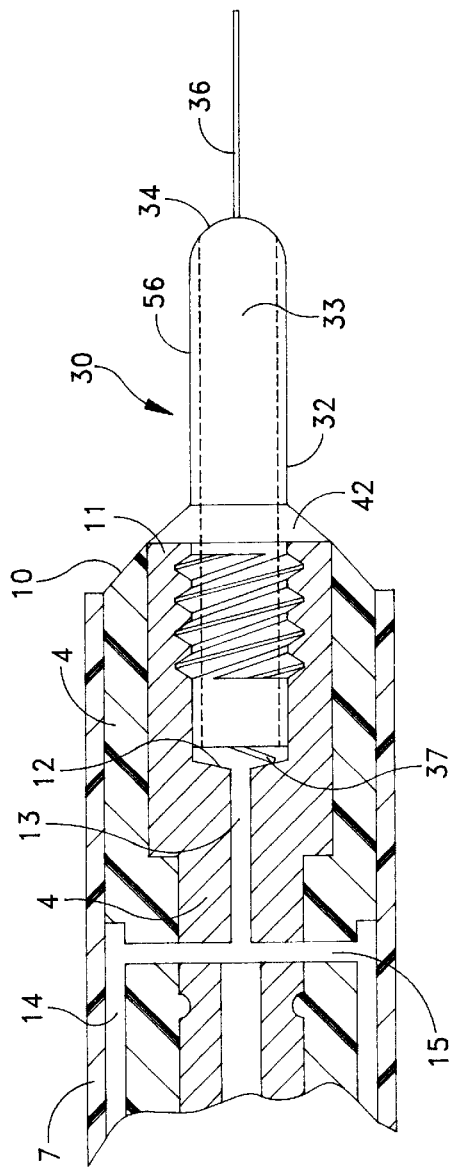
FIG. 3 is an enlarged sectional view showing the front end of the hand held portion of the electrolysis device and into which the disposable needle assembly of the present invention is inserted.

Turning now to the drawings and particularly FIG. 1 thereof, the hand held forward portion or holder of an electrolysis machine in which the disposable single use, throw away needle assembly of the present invention is mounted is depicted. Such includes an instrument holder 2 adapted to be hand held and including either an electrical or electromagnetic power source passing through a coaxial power cord 3 in turn connected to an electrolysis machine including a pressurized air source (not shown). The holder includes a body or housing 4 preferably formed from a stiff electrically insulating material such as high impact styrene plastic and includes a central passage 5 extending therethrough in which the power cord may be received. The rear end of the power cord is housed within a plastic tubing 6 dimensioned such that the power cord is spaced therefrom so that pressurized air may flow through such space from the aforementioned upstream source. The rear end of the housing includes a reduced diameter portion over which the tubing is force fit to form a connection therewith and the entire housing suitably covered with a preferably heat shrunk rubberized coating or layer 7 such as to provide a comfortable grip in the operator's hands.

The forward end of the housing includes an adapter 8 formed from an electrically conductive material such as brass to which the power cord 3 is soldered or otherwise electrically connected and extends at its forward end to the forward open end 10 of the housing 4. Such adapter includes an inwardly extending threaded socket 11 which terminates in a lower wall 12 having an air passage 13 extending rearwardly therefrom into the adapter and adapted to connect with air passage channels 14 preferably of rectangular shape that extend along the longitudinal extent of the housing 4. Such channels 14 communicate with the space between the power cord and the flexible plastic tubing surrounding such at their upstream end and terminate at their forward or downstream end adjacent the brass adapter. At such point, the channels 14 connect with radially inwardly extending passages 15 that in turn connect with the air passage 13 extending rearwardly from the rear wall of the socket and in this way insures that air flow from the electrolysis machine or other source thereof passes along the wire connecting the electrolysis machine to the handle or holder as above described and thence to the bottom wall of the socket.

Figure 4:
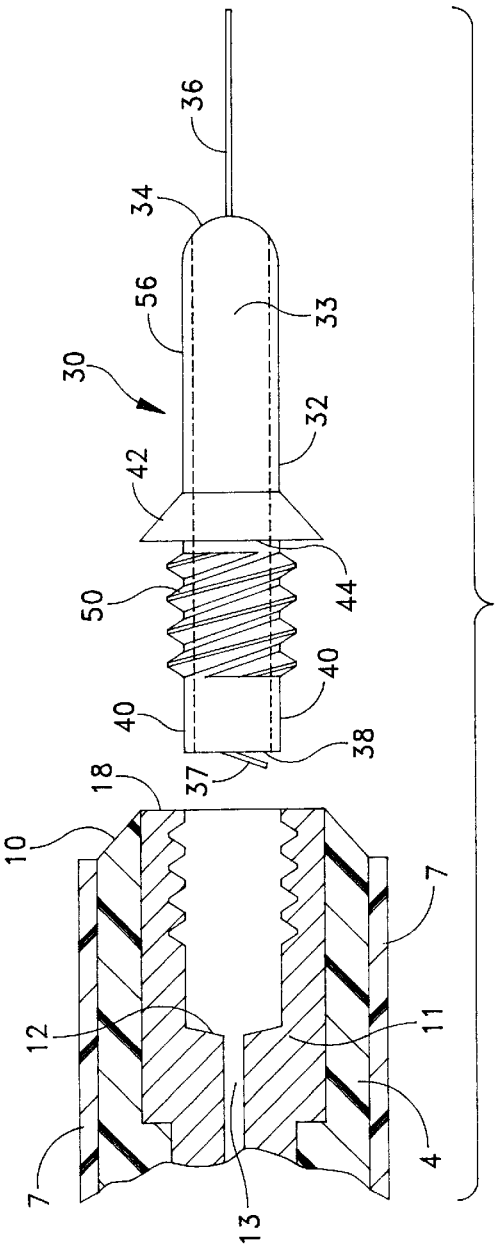
FIG. 4 is a view similar to FIG. 3 but showing the disposable needle assembly portion of the present invention removed from the hand held portion of the electrolysis machine.

Turning now to FIGS. 3 and 4 of the drawings, the relationship between the disposable needle assembly 30 of the present invention and the handle as previously described will now be more apparent. The needle assembly 30 includes a body 32 having a longitudinally extending forward portion 33 of generally configuration and terminating at its forward end in a rounded or domed type front end 34 from which the needle 36 forwardly extends. It should be brought out that the needle is embedded in the body and has a tail portion 37 extending from the rear face 38 of the shank 40 rearwardly extending from the body in order to make electrical contact with the socket of the handle or holder assembly. Intermediate the rearwardly extending shank portion and the forwardly extending portion is a flange or collar 42 preferably upwardly rearwardly extending to, in effect, form a continuation of the front end of the holder assembly as is best shown in FIG. 3 and including a rear wall 44 adapted to abut against the front face of the holder and/or of the insert embedded therein. It should be pointed out that the length of the rearwardly extending shank portion is slightly less than the length of the socket 11 of the electrically conductive insert such that there will be space between the rear wall of the shank and the bottom well of the socket such that air passing from the central channel 13 thereof will not be blocked by the rear wall of the shank. In other words, the presence of the flange in abutting contact with the forward end 18 of the socket prevents the rear wall of the shank from bottoming in the socket so as to allow air space. The flange also acts as a shield to prevent the insert socket, that is, its forward end 18, which is normally made from brass or other metallic material from contacting the fingers of the operator.

Figure 5:
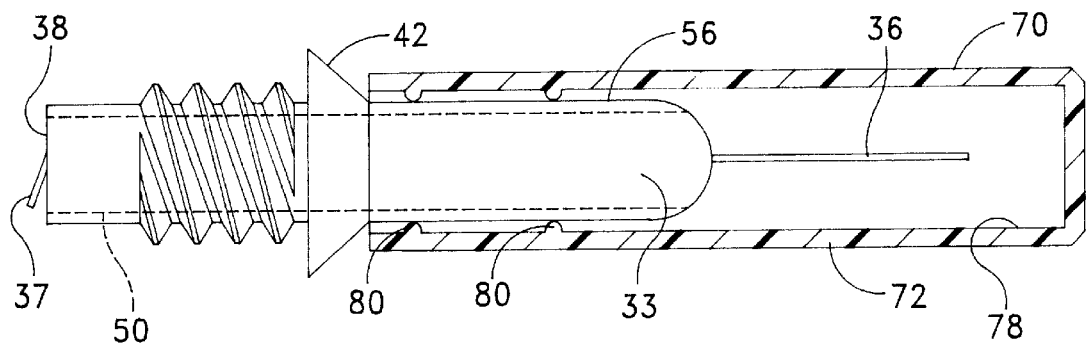
FIG. 5 is a side view showing the disposable needle assembly with the protective cap in place.
Figure 6:
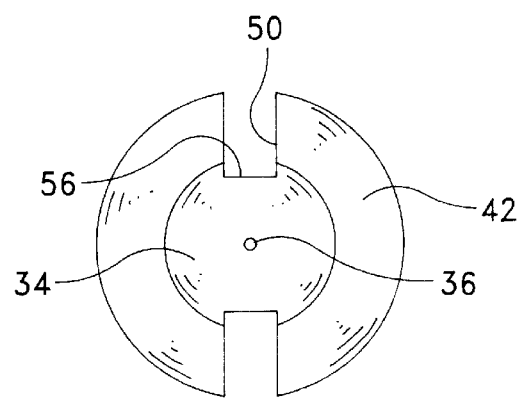
FIG. 6 is a right side view of FIG. 5 with the protective cap removed showing in particular the manner in which the air passage channels are constructed.
Figure 7:
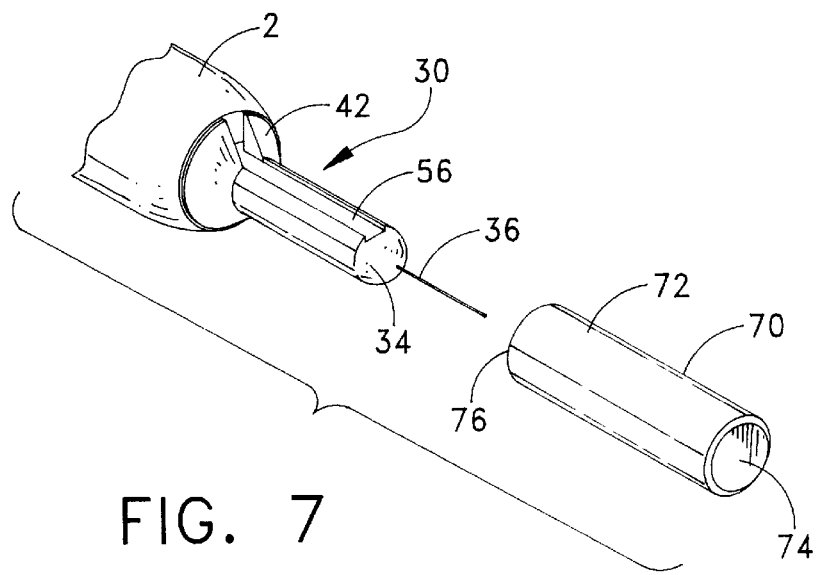
FIG. 7 is a partial perspective view similar to FIG. 3 but showing the safety cap in exploded relationship thereto.
Figure 8:
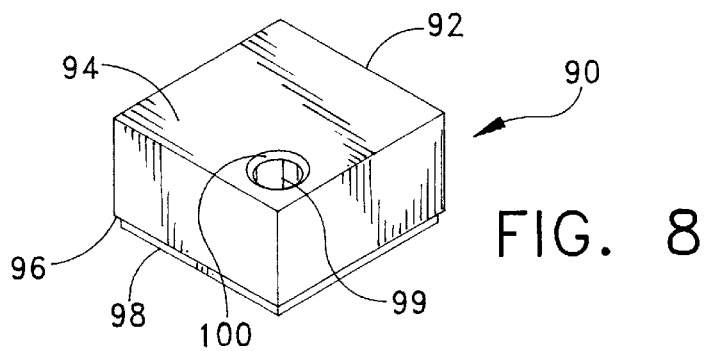
FIG. 8 is a perspective view showing the construction of a safety holder in which the safety cap may be positioned for receipt and connection with the needle assembly while attached to the electrolysis machine holder.
Figure 9A:
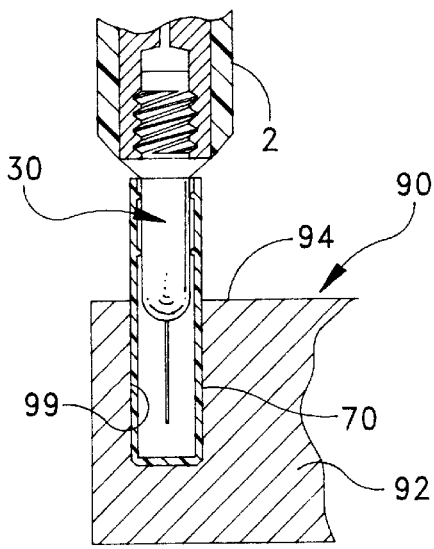
FIG. 9a is an elevational view showing the relationship of the safety cap holder and the manner in which the forward end of the electrolysis machine holder incorporating the needle assembly may be inserted thereinto.
Figure 9B:
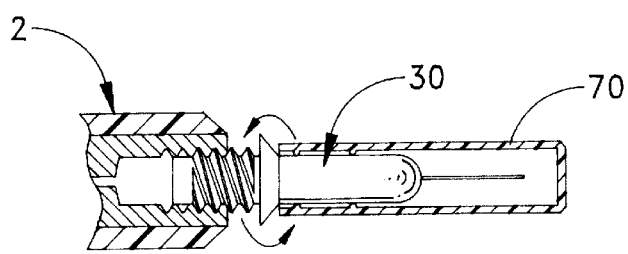
FIG. 9b shows the use of the safety cap to unscrew the disposable needle assembly from the hand held body portion of the electrolysis machine.
Figure 9C:
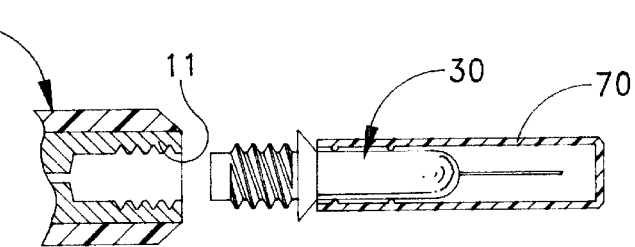
FIG. 9c shows the manner in which the safety cap while connected to the disposable needle assembly are disposed of as a unit.

Continuing with the description of the needle assembly 30, it will be apparent from not only FIGS. 3 and 4 but also FIGS. 5 through 7 that at least one and preferably a pair of diametrically opposed air channels 50 are provided that extend longitudinally along the body of the needle assembly. Such channels or slots 50 extend longitudinally along the entire length of the rear shank 40 and continue through the flange or collar 42 and may project forwardly along the forward portion 32 of the body in the form of flattened portions 56 such that air directed from the base of the insert socket follows such channels or slots 50 along the paths formed in the periphery of the body 32 and thence into contact with the skin of the person being treated. It is also preferable that the shank be threaded as depicted and received within threads provided in the insert in order to provide a secure attachment of the assembly 30 to the hand held assembly. Alternatively, a force fit such as described in my aforementioned patent may be utilized if desired. In either case, the above described air slots are required in order to provide for air penetration through and along the assembly body. Of course in those cases where air is not desired, then the necessity for such air slots is not required nor would the care taken to prevent the contact of the adjoining walls of the rear of the shank and the bottom of the insert socket be required.

Attention is now directed to FIGS. 7, 8 and 9*a* through 9*c* of the drawings in which the provision of a combination safety cap and loading/unloading tool is provided in conjunction with the needle assembly to accomplish added objectives of the present invention. Therein it will be apparent that a tubular safety cap 70 having a body wall 72, a forward closed end wall 74 and an open near or bottom end 76 formed from any suitable material but preferably formed from an at least semi-transparent and somewhat pliable plastic material is provided. Such cap 70 is of an internal diameter approximating that of the outside diameter of the forward body portion 33 of the assembly 30 such that a frictional interference fit is formed when the cap is placed thereover as shown particularly by FIGS. 5 and 7. In addition, the interior wall 78 of the cap may be provided with one or more longitudinally separated sizing rings 80 adapted to form such interference fit with the outside wall of the forward body portion. It will be apparent that the cap should also be of a length such that its open bottom end when placed over the forward end of the body will abut the collar or flange 42 and still be of an extent such that the forwardly projecting needle portion will not contact the forward cap wall so as to be bent or otherwise injured thereby.

The needle assemblies of the present invention would be normally supplied in packages in which their protective caps 70 are already fitted over the forward body portions thereof such that the cap itself is tightly engaged to the assembly and thus the cap and assembly act as a unitary assembly and can be used to manipulate the needle assembly without the need of contact with the otherwise exposed needle portion thereof. In other words, the cap provides a manipulating tool or handle for the needle assembly to which it is attached and thus can be utilized to conveniently remove such from the sales package and screw the rearwardly extending shank portion thereof into the insert socket of the hand held electrolysis handle. When such is accomplished and the needle assembly is firmly attached to the electrolysis handle, the cap can then be frictionally removed from the forward body portion by a straight longitudinal pull. In practice, it is actually desirable to adjust the specifications and tolerances of the cap and forward body portion such that it is difficult to remove the cap from the forward portion unless the shank portion of the assembly is firmly anchored as in the insert of the electrolysis handle. The recapping device of the present invention includes a fixture 90 having a body 92 and opposed upper and lower surfaces 94 and 96 with the lower surface preferably provided with some mechanism, e.g., an adhesive layer 98, to conveniently place the fixture in a convenient location next to where the electrolysis is being carried out.

The upper wall 94 includes a tubular recess 99 having an opening 100. The recess is of a depth less than that of the cap 70 such that when not being utilized to cover the front end of the needle assembly, the protective cap be placed with its open end up in the recess 100 for a purpose which will be best described in relationship to FIGS. 9*a*, 9*b* and 9*c*. Therein after the hair removal procedure has been completed or when a different needle assembly is desired, the operator takes the handle with the needle assembly attached thereto and places it such that the exposed needle as well as the forward portion of the body is projected downwardly into the open end of the cap while supported in the fixture 90 so as to frictionally attach the needle assembly thereto as previously explained. Thereafter, the operator removes the handle with both the assembly and the protective cap still attached thereto from the fixture and thereafter utilizes the safety cap to rotate the safety cap and needle assembly so as to remove such from the handle as shown in the transition between FIGS. 9*b* and 9*c* and thereafter dispose of the used needle assembly with the protective cap still attached thereto in a suitable container. Thence, another needle assembly may be screwed into the handle assembly utilizing the cap attached thereto for such purpose and the process repeated as desired. It will be apparent that the above procedure not only protects the user from contact with the projecting needle in the mounting procedure but also in the removal procedure and that the previously exposed and thus contaminated needle continues to be protected even when discarded.

While there is shown and described herein certain specific structure embodying this invention, it will be manifest to those skilled in the art that various modifications and rearrangements of the parts may be made without departing from the spirit and scope of the underlying inventive concept and that the same is not limited to the particular forms herein shown and described except insofar as indicated by the scope of the appended claims.

I claim:

1. In combination with a hand held electrolysis instrument including front and rear ends and having an insulated hand grip portion including a needle assembly receiving socket in turn having an open front and an inner lower wall in said front end, said hand grip portion further including an air passage for the receipt of pressurized air extending from the rear end to the front end thereof and exiting at an air opening proximal the lower wall of said socket, a disposable, single use, throw away electrolysis needle assembly comprising an electrical insulating body formed of a molded plastic and including a shaped forward end portion, an extremely fine uninsulated metal needle adapted to be inserted through the epidermis layer of the skin of a human patient outwardly forwardly projecting from said forward body end, said body further including a rearwardly extending shank portion in turn adapted to extend into and connect with said receiving socket, said needle assembly further including an outwardly extending flange separating said forward end portion and said shank portions, said flange having a rear surface adapted to contact the hand grip portion of the electrolysis instrument surrounding said needle assembly receiving socket and wherein said needle assembly further includes at least one radially inwardly longitudinally extending air channel communicating with said lower wall air opening such that the flow of pressurized air passing along said hand grip portion and exiting in said socket may pass unobstructively along the outer surface of said needle assembly so as to contact the skin of the human patient adjacent the contact area of the needle therewith.

2. The combination of claim 1, said needle further including a wire portion extending through said body and including a portion outwardly projecting from the shank portion thereof so as to form an electrical connection with the instrument.

3. The combination of claim 1, wherein said air channel extends continuously through both said shank and said flange.

4. The combination of claim 3, wherein there are a pair of diametrically opposed needle assembly air channels.

5. The combination of claim 1, wherein said shank includes a bottom wall in turn spaced from the socket lower wall, said air opening disposed through said socket lower wall whereby said air passage and said air channel are in operative connection with each other.

6. The assembly of claim 5, wherein the length of the shank portion extending rearwardly of said flange rear surface is less than the depth of said receiving socket whereby air passing through the air opening will not be blocked by said shank from entering said needle assembly air channel.

* * * * *